(12) United States Patent
Smith (10) Patent No.: US 8,644,579 B2
(45) Date of Patent: Feb. 4, 2014

(54) SYSTEM AND METHOD FOR DIAGNOSING ONSET OF OSTEOARTHRITIS

(75) Inventor: Gail K. Smith, Downingtown, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 849 days.

(21) Appl. No.: 12/813,317

(22) Filed: Jun. 10, 2010

(65) Prior Publication Data

US 2010/0316271 A1 Dec. 16, 2010

Related U.S. Application Data

(60) Provisional application No. 61/185,819, filed on Jun. 10, 2009.

(51) Int. Cl.
*G06K 9/00* (2006.01)

(52) U.S. Cl.
USPC .......................................... 382/132; 382/128

(58) Field of Classification Search
USPC .......................................... 600/300; 382/132
See application file for complete search history.

(56) References Cited

U.S. PATENT DOCUMENTS 5,125,043 A * 6/1992 Karlsson ...................... 382/300
5,482,055 A * 1/1996 Smith ............................ 600/595

OTHER PUBLICATIONS

Lifelong diet restriction and radiographic evidence of osteoarthritis of the hip joint in dogs, Smith, G.K., et al., JAVMA, vol. 229, No. 5, Sep. 1, 2006, pp. 690-693.*

Adams WM, et al., "Early detection of canine hip dysplasia: comparison of two palpation and five radiographic methods." 1998, *J Am Anim Hosp Assoc* 34:339-347.

Kealy RD, et al., "Effects of dietary electrolyte balance on subluxation of the femoral head in growing dogs." 1993, *Am J Vet Res* 54:555-562.

Kealy RD, et al., "Effects of limited food consumption on the incidence of hip dysplasia in growing dogs." 1992, *J Am Vet Med Assoc* 201:857-863.

Popovitch CA, et al., "Comparison of susceptibility for hip dysplasia between Rottweilers and German shepherd dogs." 1995, *J Am Vet Med Assoc* 5:648-650.

Puerto DA, et al., "Relationships between results of the Ortolani method of hip joint palpation and distraction index, Norberg angle, and hip score in dogs." 1999, *J Am Vet Med Assoc* 214:497-501.

Smith GK, et al., "Coxofemoral joint laxity from distraction radiography and its contemporaneous and prospective correlation with laxity, subjective score, and evidence of degenerative joint disease from conventional hip-extended radiography in dogs." 1993, *Am J Vet Res* 54:1021-1042.

(Continued)

*Primary Examiner* — Joseph Burgess
(74) *Attorney, Agent, or Firm* — Riverside Law LLP (57) ABSTRACT

The present invention relates to a method of diagnosing/predicting a degenerative disease in the hip of a subject. The method including the steps of applying a compressive force on at least one hip joint of the subject and calculating a compression index value for at least one hip joint, wherein a non-zero compression index value for the at least one hip joint is indicative of the subject developing/having a degenerative disease. The present invention also relates to a diagnostic test for determining incongruity in a hip joint of a subject, where the test includes the steps of applying a compressive force on at least one hip joint of the subject and calculating a compression index value, wherein a non-zero compression index value for the hip joint is indicative of at least mild hip joint incongruity.

18 Claims, 2 Drawing Sheets

(56) References Cited

OTHER PUBLICATIONS

Smith GK, et al., "New concepts of coxofemoral joint stability and the development of a clinical stress-radiographic method for quantitating hip joint laxity in the dog." 1990, *J Am Vet Med Assoc* 196:59-70.

Smith GK, et al., "Evaluation of risk factors for degenerative joint disease associated with hip dysplasia in dogs." 1995, *J Am Vet Med Assoc* 206:642-647.

Smith GK, et al., "Evaluation of risk factors for degenerative joint disease associated with hip dysplasia in German Shepherd Dogs, Golden Retrievers, Labrador Retrievers, and Rottweilers." 2001, *J Am Vet Med Assoc* 219:1719-1724.

Smith GK, et al., "Lifelong diet restriction and radiographic evidence of osteoarthritis of the hip joint in dogs." 2006, *J Am Vet Med Assoc* 229:690-693.

* cited by examiner

SYSTEM AND METHOD FOR DIAGNOSING ONSET OF OSTEOARTHRITIS

CROSS-REFERENCE TO RELATED APPLICATIONS

This application claims the benefit of priority to U.S. Provisional Application Ser. No. 61/185,819, filed Jun. 10, 2009, the entire contents of which are incorporated by reference herein as if set forth herein in its entirety.

STATEMENT REGARDING FEDERALLY SPONSORED RESEARCH OR DEVELOPMENT

This invention was made, in part, using funds obtained from the U.S. Government (Biomedical Research Support Grant, Division of Research Resources, National Institutes of Health, 1984), and the U.S. Government therefore has certain rights in this invention.

BACKGROUND OF THE INVENTION

Hip dysplasia (HD) in dogs is a developmental orthopedic disease in which abnormal development of the hip leads to functional hip laxity. This results in cartilage degradation, osteophyte formation, subchondral sclerosis, and ultimately osteoarthritis (Henricson B, et al., *J Small Anim Pract* 1966: 673-687; Smith G K., *J Am Vet Med Assoc* 1997; 210:1451-1457; Riser W H., *J Am Vet Rad Soc* 1973; 14:35-50; Jones T C, et al., *Veterinary pathology.* 6th ed. Baltimore: The Williams & Wilkns Co, 1997; 899-946; Morgan J, Wind A, Davidson A. Hip Dysplasia. In: *Hereditary bone and joint diseases in the dog: osteochondroses, hip dysplasia, elbow dysplasia.* Hannover, Germany: Schlutersche GmbH and Co, 2000; 109-208.). It is empirically believed that fibrotic thickening of the joint capsule associated with osteoarthritis in dogs with HD causes a tightening effect on a hip joint, thereby making the joint more stable (Riser W H., *J Am Vet Rad Soc* 1973; 14:35-50; Jones T C, et al., *Veterinary pathology.* 6th ed. Baltimore: The Williams & Wilkns Co, 1997; 899-946; Barr ARS, et al., *J Small Anim Pract* 1987; 28:243-252). However, in humans, osteoarthritis does not influence subluxation (joint laxity) and will affect position within the hip joint only when the femoral head is malformed (Gofton J P., *CMAJ* 1971; 104:911-915). It is further proposed that tightening and increased stability of the hip joints of affected dogs are associated with less pain. For the most seriously affected dogs, this reduction in pain is usually observed by the time dogs are 18 months old (Barr A R S, et al., *J Small Anim Pract* 1987; 28:243-252). In addition, it has been theorized that a large active muscle mass may inhibit transformation of passive laxity into functional laxity as a dog ambulates, and thus decrease the stresses on articular cartilage that lead to degenerative changes (Riser W H, et al., *Am J Vet Res* 1967; 28:769-777; Smith G K, et al., *Am J Vet Res* 1993; 54:1021-1042).

Currently, there is no cure for osteoarthritis in humans or other mammals. However, there are treatment options for osteoarthritis. For example, non-surgical treatments include use of NSAIDS and nutraceuticals, the modification of nutrition, increase exercise, and physical therapy. Surgery is also an option for end stage disease.

That said, prevention is key in the fight against canine hip dysplasia and osteoarthritis. By predicting the early stages of osteoarthritis, genetic control and selective breeding may be used as an effective means of reducing the severity of canine hip dysplasia and the development of osteoarthritis in subsequent generations of animals by avoiding mating those animals showing signs of osteoarthritis development. However, accurate prediction of osteoarthritis requires a reliable screening method implemented early in life.

Several methods have been proposed to measure passive laxity of the hip joints in humans and dogs. However, two radiographic methods, known as the Norberg angle (NA) and the Distraction index (DI) are used most commonly in the dog (Smith G K, et al., *Am J Vet Res* 1993; 54:1021-1042; Adams W M, et al., *Vet Radiol Ultrasound* 2000; 41:484-490; Adams W M, et al., *J Am Anim Hosp Assoc* 1998; 34:339-347; Owens J, et al., *Radiographic interpretation for the small animal clinician.* 2$^{nd}$ ed. Baltimore: The Williams & Wilkins Co, 1999; 82-89; Kapatkin A S, et al., *J Am Vet Med Assoc* 2004; 224:542-546; McLaughlin R Jr, et al., *Vet Med* 1996; 91:36-47; Lawson D D. *Vet Rec* 1963; 75:445-456; Lust G L, et al., *J Am Vet Med Assoc* 2001; 219:1242-1246; Popovitch C A, et al., *J Am Vet Med Assoc* 1995; 5:648-650; Smith G K, et al., *J Am Vet Med Assoc* 1990; 196:59-70; Smith G K, et al., *J Am Vet Med Assoc* 2001; 219:1719-1724; Smith G K, et al., *J Am Vet Med Assoc* 1995; 206:642-647). The NA measurement method is applied to ventrodorsal hip-extended radiographs as a means of quantifying hip joint laxity (Owens J, et al., *Radiographic interpretation for the small animal clinician.* 2$^{nd}$ ed. Baltimore: The Williams & Wilkins Co, 1999; 82-89; Olsson S. *Adv Small Anim Pract* 1961; 3:117-118). Throughout the world, the NA has been incorporated into several screening systems as a measure of joint laxity. However, in the United States, the NA is not measured; rather, joint laxity is subjectively estimated and represented as subluxation.

Another method, known as the PennHIP method (PennHIP, School of Veterinary Medicine, University of Pennsylvania, Philadelphia, Pa.), consists of three separate radiographs, namely the distraction view, compression view, and ventrodorsal hip-extended view, for full assessment of the spatial relationships of the femoral head to the acetabulum. With the dog on its back and the hip joints in a neutral, stance-phase position, the distraction radiographic view permits quantifying maximum passive hip joint laxity by use of the DI (Smith G K, et al., *Am J Vet Res* 1993; 54:1021-1042; Adams W M, et al., *J Am Anim Hosp Assoc* 1998; 34:339-347; Popovitch C A, et al., *J Am Vet Med Assoc* 1995; 5:648-650; Smith G K, et al., *J Am Vet Med Assoc* 1990; 196:59-70; Culp W T, et al., *Vet Surg* 2006; 35:453-459). The compression radiographic view is also obtained with the rear limbs in a neutral, stance-phase position. However, instead of distraction, the femoral heads are compressed into the acetabula to reveal the extent of joint congruency represented by the CI (Smith G K, et al., *J Am Vet Med Assoc* 1990; 196:59-70). For a perfectly congruent joint, the CI is zero (or within measurement error of zero). Joints that deviate substantially from zero represent grades of incongruency. The ventrodorsal hip-extended view is included in the PennHIP evaluation to help identify key landmarks to aid in accurate measurement of hip laxity appearing on the distraction radiograph and with the new information in the pending patent application, to obtain supplementary information regarding the existence of osteoarthritis in a hip joint as conventionally described. These methods are also described in U.S. Pat. No. 5,482,055, the disclosure of which is incorporated by reference herein as if set forth in its entirety herein.

Irrespective of animal positioning and measurement method or method combinations, no studies have been conducted to examine the change in laxity or congruency of a hip joint associated with the development of radiographic osteoarthritis.

Thus, there is a long felt need in the art for a diagnostic measurement to correlate with degenerative changes associated with early stages of osteoarthritis. The present invention meets this need.

SUMMARY OF THE INVENTION

The present invention provides a method of predicting a degenerative disease in the hip of a subject. The method includes the steps of applying a compressive force on at least one hip joint of the subject, and calculating a compression index value for the at least one hip joint of the subject, wherein a non-zero compression index value for the at least one hip joint is indicative of the subject developing a degenerative disease.

In one embodiment, the non-zero compression index value for the at least one hip joint is further indicative of hip joint incongruity. In another embodiment, the degenerative disease is osteoarthritis. In another embodiment, the non-zero compression index value for the at least one hip joint is indicative of osteoarthritis in the subject at or before osteoarthritis is radiographically apparent in the subject. In another embodiment, the non-zero compression index value is greater than or equal to about 0.01. In another embodiment, the non-zero compression index value is greater than or equal to about 0.03. In another embodiment, the calculating of the compression index value includes at least one radiographic image of the at least one hip joint. In another embodiment, the calculation of compression index value includes use of circle gauges on the radiographic images to find the centers of the acetabulum and centers of the femoral heads, and measuring the distance between the two centers and dividing by the radius of the femoral head. In another embodiment, the calculation further includes superimposing precision-machined circle gauges on the cortical margins (rims) of the acetabulum and femoral heads to find the respective geometric centers. In another embodiment, the calculation further includes a software program that uploads digital radiographic images to a high-resolution computer screen. In another embodiment, the subject is a canine.

The present invention also provides a test for determining incongruity in a hip joint of a subject. The test includes the steps of applying a compressive force on at least one hip joint of the subject and calculating a compression index value, wherein a non-zero compression index value for the at least one hip joint is indicative of at least mild hip joint incongruity.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIGS. 1A, 1B and 1C, depict Ventrodorsal hip-extended (A), compression (B), and distraction (C) radiographic projections of the hip joint of a representative dog. As depicted in FIG. 1A, NA is derived from the ventrodorsal hip-extended projection. It is the angle between a line connecting the femoral head centers and a line from the femoral head center to the craniodorsal acetabular rim. As depicted in FIG. 1B, circle gauges are used to determine the CI from the compression projection. In this case, the CI is equal to about zero. As depicted in FIG. 1C, circle gauges are used to determine the DI from the distraction projection. The DI and CI are calculated by dividing the measured distance between the femoral head center and acetabular center (d) by the radius (r) of the femoral head.

FIG. 2, comprising FIGS. 2A and 2B, depict compression radiographic projections of the hip joints of representative dogs illustrating a CI equal to zero (FIG. 2A) and a CI not equal to zero (FIG. 2B).

DETAILED DESCRIPTION OF THE INVENTION

The present invention encompasses methods and techniques for predicting the development of osteoarthritis in a subject at or before such changes are radiographically apparent in the subject, wherein a non-zero CI-value represents a valid early measure for the development of osteoarthritis. The present invention also encompasses methods and techniques for diagnosing hip joint incongruity, which has been identified as an early diagnostic marker for laxity and ultimately osteoarthritis.

DEFINITIONS AND ABBREVIATIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

A "subject" as used herein, is a living animal, preferably a mammal, and more preferably a canine.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A "non-zero" value, with respect to index measurements, means a value greater than zero that is not based on variability likely represented by measurement error.

The term "CI" stands for "Compression Index."
The term "DI" stands for "Distraction Index."
The term "HD" stands for "Hip dysplasia."
The term "NA" stands for "Norberg angle."
The term "ANOVA" stands for "Analysis of variance"
The term "$t_1$" stands for "Time of the first radiographic evaluation."
The term "$t_2$" stands for "Time of the second radiographic evaluation."

DESCRIPTION

As contemplated herein, the compression view of the hip joint is used as a diagnostic measurement to correlate with degenerative changes associated with early stages of osteoarthritis. According to an aspect of the present invention, a CI measurement is used to indicate osteoarthritis in a subject at or before such changes are radiographically apparent in the subject. As contemplated herein, a non-zero CI value represents a valid early measure for the development of osteoarthritis.

a. Methods of Measurement

Hip joint laxity is the most important risk factor for the development of osteoarthritis. The amount of laxity or looseness in a hip joint is related to the chance that a hip will develop osteoarthritis. Generally speaking, the looser the hip, the greater the risk.

The present invention includes a diagnostic testing method that uses radiography to identify animals with a higher risk of developing osteoarthritis of the hip, or hip dysplasia. As contemplated herein, use of the compression view, including measurement of the compression index, results in the identification of an early diagnostic marker for laxity. This is uniquely different from prior usage of the compression view, which, prior to the present invention, served only as a non-diagnostic reference point to identify critical anatomic landmarks for comparison with the distraction view and/or ventrodorsal hip-extended view. Therefore, as contemplated herein, the compression view alone may be used to predict the development of osteoarthritis of the hip before radiographic signs appear. The compression view may also be used to diagnose or indicate hip joint incongruity, which has been identified as an early diagnostic marker for laxity and ultimately osteoarthritis. Thus, by identifying those animals (particularly large breed canines) more at risk for ultimately developing osteoarthritis will enable breeders to avoid breeding animals that carry the trait.

For the measurement of hip joint laxity, the methods contemplated herein are quantitative (i.e., they assign a number to joint laxity) as opposed to being qualitative or subjective, such as providing an ordinal score (e.g. excellent, good, fair, etc.). The methods of the present invention are therefore not as vulnerable to inter- and intra-observer errors that are commonly associated with subjective measurement systems. The index method, such as the CI or DI, is calculated by superimposing precision-machined circle gauges on the cortical margins (rims) of the acetabulum and femoral heads to find the respective geometric centers. This measurement may also be performed using software that uploads digital radiographic images to a high-resolution computer screen. On the compression view, if the joint is free of osteoarthritis, the centers of the acetabulum and femoral head should coincide indicating that the joint is indeed concentric. On the distraction view, the distractive force causes separation between the centers. The distance, d, between the centers is a measure of hip joint laxity. However, d also varies with dog size (larger dogs would likely have larger d's than smaller dogs), with age of the dog, and with magnification due to variation in hip-to-film distance. To circumvent these potential sources of variation, d is normalized with respect to all sizes of femoral heads and acetabula by dividing it by the radius of the femoral head, r. The resulting index, $I=d/r$, is a unitless number ranging from 0 to 1 (or more). The laxity index computed for the compression view is called a compression index (CI), likewise, the laxity index for the distraction view is called the distraction index (DI).

As contemplated herein, a "non-zero" CI value represents at least mild hip joint incongruity, and thus indicates early osteoarthritis or other degenerative joint disease. For example, a CI greater than or equal to about 0.03 is indicative of hip joint incongruity.

In order to obtain a compression view of the hips, a subject, such as a dog, is placed in dorsal recumbency on a radiographic table, and preferably in a plastic trough. In order to maintain the dog in position throughout the procedure, weights, such as sandbags, are preferably placed over the front legs and chest. The pelvis is preferably positioned with a primary x-ray beam centered over the midline between both hips. The hocks are grasped such that the tibias are parallel to the table surface and parallel to each other, and the stifles are in approximately 90° of flexion. The femurs are approximately perpendicular to the table surface. More specifically, the femur is positioned so that, with respect to the coordinate system defined above, the hip position is between about 10° of flexion and 30° of extension, between about 10° and 30° of abduction, and between about 0 and 10° of external rotation. It should be noted that this coordinate system is with respect to the plane of the pelvis. In the dog, the plane of the pelvis is rotated approximately 15° in the flexion/extension axis from the plane of the radiographic table. Once the femur is in this position, hand-held weights are placed lateral to the hips, and slight medial pressure is applied to the greater trochanters seating the femoral heads firmly in the acetabulae. Alternatively, slightly rotating the tibiae externally, with the stifles at stance-phase distance apart, will provide enough force in the medial direction to achieve the same compressive effect. The combination of these steps results in the application of a compressive force on the hip joint. The compressive force is maintained for an interval sufficient to permit radiographic exposure. The CI and DI, as presented herein, are obtained by dividing a measurement in millimeters by the femoral head radius, also in millimeters. With reference to FIGS. 2A and 2B, circle gauges may be used on radiographic images to find the centers of the acetabulum and centers of the femoral heads. The distance between the two centers may be measured and divided by the radius of the femoral head (see FIG. 2B). For the compression view of a normal hip, this quotient should be zero.

The distraction index is a measurement of hip joint laxity, while the compression index is a measure of hip joint congruity. Hips with DIs on the distraction view that are close to 0 are considered to be tight, while DIs close to 1 are considered to be very loose. The DI is an indication of the "percent out of joint" that the femoral head is displaced from the acetabulum. For example, DI=0.58 means the femoral head comes out of the joint by 58%, DI=0.75, 75% out of joint, and so on. This also makes interpretation of the DI more intuitive: a hip with a DI=0.50 is twice as lax as a hip with a DI=0.25. To obtain proper diagnostic radiographs, the musculature around the hip should be relaxed. In the distraction radiographic view, the dog is placed in dorsal recumbency on the radiographic table, preferably in a plastic trough. The pelvis is positioned so that the primary x-ray beam is centered over the midline between the hips. The examiner grasps the hocks such that the tibias are parallel to the table surface and parallel to each other, and the stifles are in approximately 90° of flexion. The femurs are positioned so that the hip joint is between about 10° of flexion and 30° extension, between about 10 and 30° of abduction, and from about 0 to 10° of external rotation. Within this range of positioning, it has been found that the mean percentage of maximal hip laxity may be greater than about 90 percent. Preferably, the hip joint position is about 10° externally rotated, is about 10° of extension and about 20° of abduction. At this position, maximal hip laxity is observed. This may be accomplished by grasping the hocks such that the tibias are parallel to the table surface and parallel to each other, and the stifles are in about 90° of flexion with the femur perpendicular to the table. It should also be noted that the plane of the table is rotated about 15° in the flexion/extension axis, from the plane of the pelvis. Once the hip joint is in that position, a substantially lateral outward force, or distractive force, is applied to each femoral head. In a preferred technique, this is accomplished by applying an inward force near the knee and rotating each femur about a point intermediate the femoral head and the knee, thereby forcing femoral head outward.

b. Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods employed in the experiments disclosed hereinbelow are now described:

Labrador Retrievers that had at least two PennHIP radiographic evaluations were identified in the PennHIP database. Inclusion criteria required that: all dogs were ≥16 weeks of age, dogs had no evidence of radiographic osteoarthritis at $t_1$, and the minimum interval between radiographic sessions (ie, $t_1$ and $t_2$) was about two months. The existence of radiographic evidence of osteoarthritis of the hip joints was determined and based on the evaluation in accordance with the standard radiographic protocol based on Orthopedic Foundation for Animals-type scoring (Morgan J, Wind A, Davidson A. Hip Dysplasia. In: *Hereditary bone and joint diseases in the dog: osteochondroses, hip dysplasia, elbow dysplasia*. Hannover, Germany: Schlutersche GmbH and Co, 2000; 109-208; Owens J, et al., *Radiographic interpretation for the small animal clinician*. 2$^{nd}$ ed. Baltimore: The Williams & Wilkins Co, 1999; 82-89; Lopez M J, et al., *Am J Vet Res* 2008; 69:362-370). None of the dogs had prior injuries, surgery, or evidence of cavitation.

From this initial sample of dogs, two groups were selected. Twenty dogs were identified that had radiographic evidence of osteoarthritis at a subsequent evaluation (ie, at $t_2$). These 20 dogs comprised the osteoarthritis group, as described herein. A larger number of dogs were identified that did not have radiographic evidence of osteoarthritis at $t_2$ (non-osteoarthritis dogs); the non-osteoarthritis dogs were matched with dogs in the osteoarthritis group on the basis of sex and age (+2 months). Thus, there were also 20 dogs in the non-osteoarthritis group.

Figure 1:
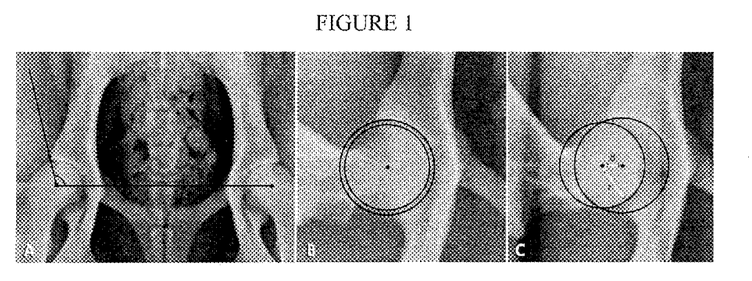
Figure 2:
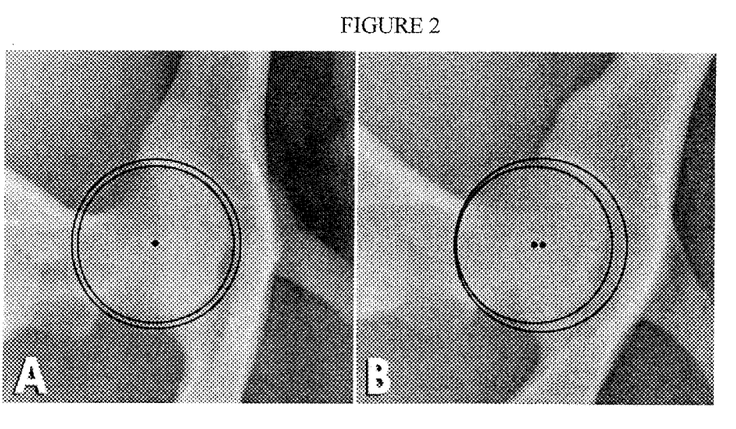

As depicted in FIG. 1, distraction, compression, and ventrodorsal hip-extended radiographs from $t_1$ and $t_2$ were used in the measurement of DI, CI, and NA, respectively. While the NA and DI are measures of hip joint laxity, the CI is a measure of joint congruity, as depicted in FIG. 2. For statistical analysis, the worst hip in each dog (ie, dog with the greater DI) was determined at $t_1$. The same hip was then measured again at $t_2$. The DI measurements were obtained from the PennHIP database. However, CI and NA were not included in the PennHIP database; therefore, measurements for those variables (Smith G K, et al., *Am J Vet Res* 1993; 54:1021-1042) were generated by an experienced evaluator.

A repeated-measures analysis of variance (ANOVA) with post-hoc pairwise comparisons (least significant difference) was used to test for mean differences in NA, DI, and CI measurements within subjects at $t_1$ and $t_2$, and differences between the non-osteoarthritis and osteoarthritis groups for all measurement methods at each time period (time was the repeated measure within subjects). A repeated-measures ANOVA was performed separately for each measurement method. In addition, t-tests were used to compare mean age and body weight between groups at each radiographic evaluation ($t_1$ and $t_2$). For all analyses, significance was set at values of $P<0.05$. All analyses were performed with statistical software (SPSS 12.0 for Windows, SPSS, Chicago, Ill.; SAS, version 9.1, SAS Institute Inc, Cary, N.C.).

The results of the experiments presented in the following Examples are now described:

As depicted in Table 1, descriptive statistics for age of the non-osteoarthritis (n=20 dogs) and osteoarthritis (20) groups at $t_1$ and $t_2$ and the difference in age of dogs between the 2 time periods ($t_2-t_1$) was determined, where values are reported in number of years. There was no significant difference in mean age between the non-osteoarthritis (0.47 years) and osteoarthritis (0.46 years) groups at $t_1$. There was a significant ($P=0.002$) difference in mean age between the non-osteoarthritis (1:41 years) and osteoarthritis (1.00 years) groups at $t_2$. The mean difference for the interval from $t_1$ to $t_2$ was about 0.94 years for the non-osteoarthritis group and about 0.54 years for the osteoarthritis group. The longer interval for the non-osteoarthritis group was intentional to allow additional time for osteoarthritis to develop in those dogs.

TABLE 1

| Group | $t_1$ | | | $t_2$ | | | $t_2 - t_1$ | | |
| --- | --- | --- | --- | --- | --- | --- | --- | --- | --- |
| | Min | Max | Mean ± SD | Min | Max | Mean ± SD | Min | Max | Mean ± SD |
| Non-osteoarthritis | 0.35 | 0.68 | 0.47 ± 0.08 | 1.00 | 2.20 | 1.41 ± 0.50 | 0.51 | 1.84 | 0.94 ± 0.50 |
| Osteorarthritis | 0.39 | 0.68 | 0.46 ± 0.09 | 0.59 | 1.50 | 1.00 ± 0.20 | 0.20 | 0.97 | 0.54 ± 0.18 |

As depicted in Table 2, descriptive statistics for body weight of the non-osteoarthritis (n=20 dogs) and osteoarthritis (20) groups at $t_1$ and $t_2$ and the difference in body weight of dogs between the 2 time periods ($t_2-t_1$) were determined, where values are reported in kilograms. There was no difference in mean body weight between the non-osteoarthritis and the osteoarthritis groups at $t_1$ (17.30 kg and 18.00 kg, respectively) or $t_2$ (25.50 kg and 26.34 kg, respectively). Mean weight gain in the interval from $t_1$ to $t_2$ was about 8.20 kg for the non-osteoarthritis group and about 8.76 kg for the osteoarthritis group.

TABLE 2

| Group | $t_1$ | | | $t_2$ | | | $t_2 - t_1$ | | |
| --- | --- | --- | --- | --- | --- | --- | --- | --- | --- |
| | Min | Max | Mean ± SD | Min | Max | Mean ± SD | Min | Max | Mean ± SD |
| Non-osteoarthritis | 12.27 | 25.45 | 17.30 ± 3.78 | 18.64 | 32.73 | 25.50 ± 3.40 | −1.36 | 15.91 | 8.20 ± 4.22 |
| Osteoarthritis | 12.27 | 26.81 | 18.00 ± 4.70 | 19.55* | 40.91* | 26.34 ± 5.92* | −2.27* | 19.55* | 8.76 ± 5.30* |

*Represents results for only 19 dogs.

As depicted in Table 3, descriptive statistics for each measurement method within each treatment group (n=20 dogs/group) at each time period ($t_1$ and $t_2$) and the difference in values between the two time periods ($t_2-t_1$) were determined.

TABLE 3

| Measurement method | Group | $t_1$ | | | $t_2$ | | | $t_2 - t_1$ | | |
| --- | --- | --- | --- | --- | --- | --- | --- | --- | --- | --- |
| | | Min | Max | Mean ± SD | Min | Max | Mean ± SD | Min | Max | Mean ± SD |
| NA (°) | Non-osteoarthritis | 90 | 113 | 102.20 ± 5.05* | 89 | 112 | 102.28 ± 5.51* | −11 | 11 | −0.08 ± 5.38 |
| | Osteoarthritis | 84 | 104 | 96.43 ± 6.35 | 75 | 104 | 90.85 ± 8.84 | −13 | 19 | 5.558 ± 7.36 |
| DI | Non-osteoarthritis | 0.33 | 0.62 | 0.50 ± 0.09* | 0.23 | 0.68 | 0.48 ± 0.14* | −0.10 | 0.20 | 0.09 ± 0.09 |
| | Osteorarthritis | 0.48 | 0.92 | 0.70 ± 0.01 | 0.42 | 0.86 | 0.72 ± 0.10 | −0.30 | 0.20 | −0.03 ± 0.14 |
| CI | Non-osteoarthritis | 0.00 | 0.04 | 0.00 ± 0.003 | 0.00 | 0.09 | 0.01 ± 0.028* | −0.09 | 0.00 | −0.01 ± 0.024 |
| | Osteorarthritis | 0.00 | 0.17 | 0.03 ± 0.047 | 0.00 | 0.25 | 0.12 ± 0.080 | −0.25 | 0.08 | −0.09 ± 0.090 |

*Within a time period within a measurement method, value differs significantly (P < 0.05) from the value for the osteoarthritis group.

There was no significant difference in mean NA for the non-osteoarthritis group between $t_1$ and $t_2$ (102.20° and 102.28°, respectively). For the osteoarthritis group, mean NA at $t_2$ (90.85°) was significantly (P<0.001) less than the mean NA at $t_1$ (96.43°). Mean NA for the non-osteoarthritis group was significantly greater than the mean NA for the osteoarthritis group at $t_1$ (non-osteoarthritis, 102.20°; osteoarthritis, 96.43° [P<0.001]) and at $t_2$ (non-osteoarthritis, 102.43°; osteoarthritis, 90.85°; [P<0.001]).

There was no significant difference in mean DI between $t_1$ and $t_2$ for the non-osteoarthritis (0.50 vs 0.48, respectively) or osteoarthritis (0.70 vs 0.72, respectively) groups. Mean DI for the non-osteoarthritis group was significantly less than the mean DI for the osteoarthritis group at $t_1$ (non-osteoarthritis, 0.50; osteoarthritis, 0.70 [P<0.001]) and $t_2$ (non-osteoarthritis, 0.48; osteoarthritis, 0.72 [P<0.001]).

There was no significant difference in mean CI for the non-osteoarthritis group between $t_1$ and $t_2$ (0.00 and 0.01, respectively). For the osteoarthritis group, mean CI at $t_2$ (0.12) was significantly (P<0.001) greater than the mean CI at $t_1$ (0.03). No significant difference in mean CI was found between the osteoarthritis and non-osteoarthritis groups at $t_1$; however, the mean CI of the non-osteoarthritis group at $t_2$ (0.01) was significantly (P<0.001) less than the mean CI of the osteoarthritis group at $t_2$ (0.12).

Based on the experimental data presented herein, the common belief that hip joints tighten as a result of progressing osteoarthritis could not be confirmed. Joint laxity (as measured in various manners) can precede hip joint remodeling and osteoarthritis (Henricson B, et al., *J Small Anim Pract* 1966:673-687; Smith G K, et al., *J Am Vet Med Assoc* 1990; 196:59-70; Smith G K, et al., *J Am Vet Med Assoc* 1995; 206:642-647; Schnelle G B. *Univ Pa Bull* 1937; 65:15-16). Joint laxity is also a function of coxofemoral position, with measured laxity decreasing for hip joints in extreme extended positions and maximal for hip joints in more neutral positions (Heyman S J, et al., *Am J Vet Res* 1993; 54:210-215). Two methods for radiographic measurement of laxity were used herein (NA from the hip-extended radiographic projections and DI from the hip-neutral distraction radiographic projections), each of which revealed a different result. The NA is a method to quantify laxity in ventrodorsal hip-extended radiographs, where scores greater than about 105° represent tight hip joints, and lower scores represent looser hip joints (Owens J, et al., *Radiographic interpretation for the small animal clinician.* $2^{nd}$ ed. Baltimore: The Williams & Wilkins Co, 1999; 82-89). For the non-osteoarthritis group, five dogs (25%) had an NA≥105° at $t_1$ and eight (40%) dogs had an NA≥105° at $t_2$. For the osteoarthritis group, none of the dogs had an NA≥105° for either time period. The NA decreased over time in the osteoarthritis group, meaning that hip joints loosened with the onset of osteoarthritis, a finding opposite to popular belief.

The DI quantifies hip joint laxity as measured by the PennHIP DI. Scores range from 0 to >1, with 0 representing full congruency (tight hip joints) and 1 representing complete luxation (loose hip joints). As illustrated herein, the DI as a measure of joint laxity did not have a significant change over time in the non-osteoarthritis or osteoarthritis groups, which is consistent with results in other reports (Smith G K, et al., *Am J Vet Res* 1993; 54:1021-1042). This result can be interpreted to mean that in the neutral distraction position, the DI is unaffected by mild or moderate osteoarthritis. This would give the DI more clinical value (ie, the magnitude of the DI can reflect the inherent susceptibility of a dog to osteoarthritis by remaining constant despite osteoarthritis, whether evaluated prospectively or retrospectively after radiographic evidence of osteoarthritis (Smith G K, et al., *Am J Vet Res* 1993; 54:1021-1042; Smith G K, et al., *J Am Vet Med Assoc* 2001; 219:1719-1724)). Another important consideration is that the more constant a trait is over time, the higher its genetic determination and estimate of heritability (Falconer D S, *Introduction to quantitative genetics.* New York: Longman Scientific & Technical, 1996; 160-183).

The NA from the hip-extended radiographs and the DI from the distraction radiographs are both accepted measures of hip joint laxity, but these measures behaved differently in response to the onset of osteoarthritis. A constant was that both NA and DI indicated that the non-osteoarthritis dogs had tighter hip joints than did the dogs that ultimately developed osteoarthritis. This is consistent with the current understanding that hip joint laxity makes hips susceptible to osteoarthritis (Smith G K, et al., *Am J Vet Res* 1993; 54:1021-1042; Adams W M, et al., *J Am Anim Hosp Assoc* 1998; 34:339-347; Popovitch C A, et al., *J Am Vet Med Assoc* 1995; 5:648-650; Smith G K, et al., *J Am Vet Med Assoc* 1990; 196:59-70; Smith G K, et al., *J Am Vet Med Assoc* 2001; 219:1719-1724; Smith G K, et al., *J Am Vet Med Assoc* 1995; 206:642-647; Puerto D A, et al., *J Am Vet Med Assoc* 1999; 214:497-501). Interestingly, the non-osteoarthritis group had a mean DI of 0.50, which was typical for Labrador Retrievers in the PennHIP database, whereas the osteoarthritis group had a mean DI of 0.70, which was markedly greater (ie, more lax). However, both DI values were well within the osteoarthritis susceptibility range, which suggested that most of the dogs in this study may have developed osteoarthritis if monitored for a sufficient period, as reported elsewhere (Smith G K, et al., *J Am Vet Med Assoc* 2006; 229:690-693). No similar comparisons of the predictive value of NA can be made, because such studies directly relating NA to osteoarthritis susceptibility in the long term have not been performed. Another consistency was the observation that both NA and DI remained relatively constant for the non-osteoarthritis group between $t_1$ and $t_2$.

In contrast, the magnitude of NA and DI differed with regard to osteoarthritis onset. Analysis of the NA revealed that hip joints got looser with osteoarthritis onset. However, hip joint laxity as measured by the DI did not reveal changes over time in the non-osteoarthritis or osteoarthritis group, consistent with results in other reports (Smith G K, et al., *Am J Vet Res* 1993; 54:1021-1042). Of the three radiographic measurements, the DI was least affected by osteoarthritis, which provided the DI with greater clinical value as a metric reflecting osteoarthritis susceptibility (Smith G K, et al., *J Am Vet Med Assoc* 1990; 196:59-70). In contrast, the NA derived from hip-extended radiographs can have greater variability as a measure of hip joint laxity as young dogs age, which makes it a less reliable metric (Smith G K, et al., *Am J Vet Res* 1993; 54:1021-1042). As illustrated herein, a change in mean NA of 5.6° at $t_2$ was associated with the onset of osteoarthritis. This was a significant change. On the basis of the literature, it is known that a change of this magnitude is also clinically relevant. A difference in NA of 5° (ie, greater laxity) correlates with a higher likelihood of the development of HD in dogs (Smith G K, et al., *Am J Vet Res* 1993; 54:1021-1042; Kealy R D, et al., *Am J Vet Res* 1993; 54:555-562; Kealy R D, et al., *J Am Vet Med Assoc* 1992; 201:857-863). It is not known which of the two NA scores (before or after onset of osteoarthritis) is a more accurate indication of the genotype and, therefore, the breeding value of a dog.

The mean CI for the non-osteoarthritis group did not change significantly over time, which indicated that hip joint congruency was maintained throughout the time course of the study. On the other hand, the CI for the osteoarthritis group increased with progressing osteoarthritis. A non-zero CI indicates that the joint is no longer concentric, and therefore, femoral head-to-acetabular congruency has decreased. For the non-osteoarthritis group, the mean CI difference remained close to, but not exactly equal to zero. The small non-zero variability likely represented measurement error rather than a biological phenomenon, and it indicated that basic congruency was maintained over time. However, within the osteoarthritis group the CI measurements were greater at $t_2$ with development of osteoarthritis, compared with the values at $t_1$ when there was no osteoarthritis (in excess of expected measurement error). This indicated that hip joints lost congruency with development of osteoarthritis. Specifically, as the hip joints were remodeled, the center of rotation of the femoral head moved away laterally from the center of rotation of the acetabulum as an effect of the development of osteoarthritis. The change over time for the non-osteoarthritis group was smaller, compared with results for the osteoarthritis group, which indicated consistent congruency between time points. The small but non-zero CI measurements at $t_1$ for the osteoarthritis group (CI, 0.03) suggests mild hip joint incongruity before osteoarthritis is radiographically evident. A theory has been advanced that HD develops only if a young growing dog has instability and incongruity of the hip joints (Riser W H., *J Am Vet Rad Soc* 1973; 14:35-50). The data provided herein supports such a theory, and shows that the CI may be useful as a metric, either separately or in combination with the DI measurement, for predicting osteoarthritis susceptibility in growing dogs before the overt onset of radiographic evidence of osteoarthritis.

The present invention as described herein challenges the popular belief that there is compensatory tightening of the hip joints with progressive osteoarthritis. On the contrary, radiographic evidence of osteoarthritis was associated with measured loosening of the hip joints (as determined by evaluation of the NA) and incongruency (as determined by evaluation of the CI) because the femoral head no longer resided in its normal position within the acetabulum. Non-osteoarthritis dogs appeared to have hip joints that were tighter and more congruent, compared with the hip joints of osteoarthritis dogs, which is consistent with current beliefs about HD. As contemplated herein, the CI measurement may be used to correlate with degenerative changes, even before such changes are radiographically apparent. Thus, as non-zero CI values represent a valid early measure for the development of osteoarthritis, the CI measurement can be an early radiographic indicator of osteoarthritis or other degenerative joint disease.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of predicting a degenerative disease in a hip of a canine, comprising:
    applying a compressive force on at least one hip joint of the canine;
    obtaining at least one radiographic image of the at least one hip joint;
    determining, via computer software, centers of the acetabulum and centers of the femoral heads from the at least one radiographic image;
    measuring, via computer software, the distance between the acetabulum and the femoral head centers from the at least one radiographic image;
    calculating, via computer software, a compression index value for the at least one hip joint of the canine by dividing the distance between the acetabulum and the femoral head centers by the radius of the femoral head;
    determining the at least one hip joint of the canine is developing a degenerative disease or is at risk for developing a degenerative disease based on a non-zero compression index value.

2. The method of claim 1, wherein the non-zero compression index value for the at least one hip joint is further indicative of hip joint incongruity.

3. The method of claim 1, wherein the degenerative disease is osteoarthritis.

4. The method of claim 3, wherein the non-zero compression index value for the at least one hip joint is indicative of osteoarthritis in the subject at or before osteoarthritis is radiographically apparent in the subject.

5. The method of claim 1, wherein the non-zero compression index value is greater than or equal to about 0.01.

6. The method of claim 1, wherein the non-zero compression index value is greater than or equal to about 0.03.

7. The method of claim 1, wherein the calculation of compression index value comprises use of circle gauges on the radiographic images to find the centers of the acetabulum and centers of the femoral heads.

8. The method of claim 7, wherein the calculation further comprises superimposing precision-machined circle gauges on the cortical margins (rims) of the acetabulum and femoral heads to find the respective geometric centers.

9. The method of claim 7, wherein the calculation further comprises a software program that uploads digital radiographic images to a high-resolution computer screen.

10. A method for determining incongruity in a hip joint of a canine, comprising:
    applying a compressive force on at least one hip joint of the canine;
    obtaining at least one radiographic image of the at least one hip joint;
    determining, via computer software, centers of the acetabulum and centers of the femoral heads from the at least one radiographic image;
    measuring, via computer software, the distance between the acetabulum and the femoral head centers from the at least one radiographic image;
    calculating, via computer software, a compression index value for the at least one hip joint of the canine by dividing the distance between the acetabulum and the femoral head centers by the radius of the femoral head;
    determining the at least one hip joint of the canine has at least mild hip joint incongruity based on a non-zero compression index value.

11. The method of claim 10, wherein the non-zero compression index value is greater than or equal to about 0.01.

12. The method of claim 10, wherein the non-zero compression index value is greater than or equal to about 0.03.

13. The method of claim 10, wherein the indication of hip joint incongruity is further indicative of a developing degenerative disease.

14. The method of claim 13, wherein the developing degenerative disease is osteoarthritis.

15. The method of claim 14, wherein the non-zero compression index value for the at least one hip joint is further indicative of osteoarthritis in the subject at or before osteoarthritis is radiographically apparent in the subject.

16. The method of claim 10, wherein the calculation of compression index value comprises use of circle gauges on the radiographic images to find the centers of the acetabulum and centers of the femoral heads.

17. The method of claim 16, wherein the calculation further comprises superimposing precision-machined circle gauges on the cortical margins (rims) of the acetabulum and femoral heads to find the respective geometric centers.

18. The method of claim 16, wherein the calculation further comprises a software program that uploads digital radiographic images to a high-resolution computer screen.

* * * * *